(12) United States Patent
Teague et al.

(10) Patent No.: US 7,588,576 B2
(45) Date of Patent: Sep. 15, 2009

(54) BONE PLATE HOLDER AND SCREW GUIDE

(76) Inventors: Michael Teague, P.O. Box 50249, Jacksonville, FL (US) 32250; Peter Bohrmann, Mozartstrasse 24, Muhlheim (DE) D-78570

( * ) Notice: Subject to any disclaimer, the term of this patent is extended or adjusted under 35 U.S.C. 154(b) by 169 days.

(21) Appl. No.: 10/998,906

(22) Filed: Nov. 29, 2004

(65) Prior Publication Data

US 2005/0124990 A1 Jun. 9, 2005

Related U.S. Application Data

(60) Provisional application No. 60/528,262, filed on Dec. 9, 2003.

(51) Int. Cl.
*A61B 17/88* (2006.01)

(52) U.S. Cl. .................... 606/86 B; 606/280

(58) Field of Classification Search .................. 606/53, 606/60–61, 69–73, 99, 104, 86 A, 86 B
See application file for complete search history.

(56) References Cited

U.S. PATENT DOCUMENTS

| | | | | |
|---|---|---|---|---|
| 2,825,329 A * | 3/1958 | Caesar | ........................ | 606/71 |
| 2,846,744 A * | 8/1958 | Becker | ........................ | 24/108 |
| 3,724,022 A * | 4/1973 | Alberti et al. | ................... | 16/45 |
| 3,896,500 A * | 7/1975 | Rambert et al. | ............ | 623/13.14 |
| 4,020,734 A * | 5/1977 | Bell | ............................ | 411/10 |
| 4,794,918 A * | 1/1989 | Wolter | ......................... | 606/69 |
| 4,948,083 A * | 8/1990 | McNaney et al. | ............ | 248/514 |
| 5,147,361 A | 9/1992 | Ojima et al. | | |
| 5,423,826 A | 6/1995 | Coates et al. | | |
| 5,431,135 A * | 7/1995 | Tyler | ......................... | 123/185.3 |
| 5,445,641 A | 8/1995 | Frigg et al. | | |
| 5,462,547 A * | 10/1995 | Weigum | ........................ | 606/65 |
| 5,475,944 A * | 12/1995 | Mathews | .................... | 43/57.3 |
| 5,518,238 A * | 5/1996 | Hu et al. | ...................... | 473/589 |
| 5,722,976 A * | 3/1998 | Brown | ........................ | 606/69 |
| 5,732,992 A | 3/1998 | Mauldin | | |
| 5,916,200 A * | 6/1999 | Eppley et al. | ............... | 604/178 |
| 5,957,927 A | 9/1999 | Magee et al. | | |
| 6,093,201 A * | 7/2000 | Cooper et al. | ............... | 606/232 |
| 6,187,009 B1 * | 2/2001 | Herzog et al. | ................. | 606/75 |
| 6,217,468 B1 * | 4/2001 | Goodwin | ..................... | 473/588 |
| 6,235,058 B1 * | 5/2001 | Huene | ...................... | 623/13.14 |
| 6,328,746 B1 | 12/2001 | Gambale | | |
| 6,371,958 B1 * | 4/2002 | Overaker | ..................... | 606/72 |
| 6,406,478 B1 * | 6/2002 | Kuo | ............................. | 606/71 |
| 6,419,700 B2 * | 7/2002 | Huene | ...................... | 623/13.14 |
| 6,989,034 B2 * | 1/2006 | Hammer et al. | ........... | 623/23.72 |
| 2002/0147453 A1 * | 10/2002 | Gambale | ...................... | 606/71 |
| 2003/0225459 A1 * | 12/2003 | Hammer et al. | ........... | 623/23.72 |
| 2004/0019353 A1 * | 1/2004 | Freid et al. | .................... | 606/69 |
| 2004/0034354 A1 * | 2/2004 | Paul | ............................. | 606/70 |
| 2004/0097942 A1 * | 5/2004 | Allen et al. | ................... | 606/72 |
| 2004/0117016 A1 * | 6/2004 | Abramson | ............... | 623/16.11 |
| 2005/0148241 A1 * | 7/2005 | Kohen | ........................ | 439/620 |

* cited by examiner

*Primary Examiner*—Eduardo C Robert
*Assistant Examiner*—David Comstock
(74) *Attorney, Agent, or Firm*—Thomas C. Saitta (57) ABSTRACT

A holder for an osteosynthesis fixation device or bone plate and the screws or other mechanical fasteners for affixing the bone plate to bone matter, the holder temporarily retaining the bone plate and screws during the affixation procedure and providing guide bores to properly align the driver tool and the screws during insertion. The holder is significantly thicker than the bone plate, such that it is easily grasped and manipulated by the surgeon.

46 Claims, 7 Drawing Sheets

BONE PLATE HOLDER AND SCREW GUIDE

This application claims the benefit of U.S. Provisional Patent Application Ser. No. 60/528,262, filed Dec. 9, 2003, the disclosure of which is incorporated herein by reference.

BACKGROUND OF THE INVENTION

This invention relates generally to the field of bone osteosynthesis fixation devices, often referred to simply as bone plates, that are used to join two disconnected bone pieces, as well as associated devices or accessories. More particularly, the invention relates to holders or mounts for bone plates and bone screws, as well as to guide devices for properly locating and orienting the bone screws relative to the bone plate and the bone.

In certain operations, such as for example a craniotomy or a cranioplasty, the surgeon drills one or more holes or removes a portion of the skull to expose the brain. At the end of the surgical procedure, the removed portion of the skull is replaced and then secured to the surrounding bone material by mechanical fastening means called bone plates or neuroplates. The bone plates extend across the kerf or gap between the skull and the removed portion, across the bone holes themselves, or across both. The plates are relatively thin, laterally extended, rigid members that are sized to span the junction between the skull flap and the cranium. Each plate contains at least two and preferably more than two screw-receiving apertures to receive preferably self-tapping or self-drilling screws, the screws being rotationally driven into the bone material comprising the cranium and flap to secure the bone plate in place. Other types of mechanical fasteners, such as rivets or tacks for example, may also be utilized. Bone osteosynthesis fixation devices may also be required in other anatomical locations, such as for example on the jaw, chin, spine or long bones. Bone plates may be of many varied configurations, such as for example, linear, curved, T-shaped, Y-shaped, triangular, rectangular, square, circular or disk-shaped. The particular configuration required is dictated by the location and type of the bone pieces to be joined.

The bone plates are usually relatively small dimensionally, and the bone screws for affixing the plates to the bone material are very tiny. For example, a representative bone plate used in cranial applications can be only about 2 cm in diameter and will be affixed with bone screws less than 5 mm in length. Because of this, handling the bone plates and screws during the fixation procedure is often difficult. The bone plates must be properly located by the surgeon and held in place by forceps or the like while the tiny screws, also held by forceps or retention means incorporated on the driver means, are inserted into screw apertures on the bone plate and then driven into the bone material. It is not uncommon for screws to be lost or dropped during this procedure, which then requires re-sterilization of the screws or replacement. In a worse case scenario, the screws may be dropped into the exposed surgical region where recovery may be difficult. Another problem with current methodology is that the screws may driven into the bone material at improper angles, reducing the effectiveness of the fixation or resulting in improper seating in the bone plate.

It is an object of this invention to provide a holder device that addresses the problems associated with known bone plate and screw fastening systems, wherein the holder device provides a means to temporarily retain both the bone plate and the bone screws during the affixation procedure, is an easily graspable member, being relatively thick in comparison to the bone plate, and provides screw guide means to insure that the screws or other type fasteners are properly oriented when inserted into the bone material.

SUMMARY OF THE INVENTION

The invention comprises a bone osteosynthesis fixation means (e.g., a bone plate) holder device or system that temporarily retains both a bone plate adapted for affixation to bone material and the bone screws or similar mechanical fasteners for securing the bone plate to the bone material, as well as providing alignment or guide means to properly orient the screws during insertion into the bone material. The bone plate may be of various configurations, including for example linear, T-shaped, Y-shaped, triangular, rectangular, square, circular or disk-shaped, and may be planar, angled, curved or contoured.

The holder device is relatively thick in comparison to the thickness of the bone plate, such that the holder may be easily grasped by the surgeon during the affixation procedure. The bone plate is releasably mounted to the bottom of the holder, preferably by mechanical interlock or press-fit means, and the screws are retained within passageways or bores accessible to the screw driving means, such as a screwdriver, from the top of the holder, the bores and screws being aligned with screw apertures disposed in the bone plate. Once the bone plate is properly located and the screws are driven to secure the plate to the bone material, the holder is removed from the bone plate.

DETAILED DESCRIPTION OF THE INVENTION

With reference to the drawings, the invention will now be described with regard for the best mode and the preferred embodiments. In general, the invention is a bone plate holder that temporarily retains a bone plate and the mechanical fasteners for securing the bone plate to the bone, wherein the mechanical fasteners are retained within or aligned with guide passageways or bores such that the surgeon can properly position the bone plate by grasping the bone plate holder and accurately drive the mechanical fasteners through the plate and into the bone, then can easily remove the holder from the affixed bone plate.

The invention, as shown in the embodiment of FIGS. 1 through 4, is a bone plate holder 10 comprising a main body 11 having a top 12, bottom 13 and sides 14. An annular shoulder 15 for better grasping of the holder 10 may also be provided. Provided on or adjacent the bottom 13 is plate retainer means 20 for temporarily retaining a bone plate 30.

Bone plate 30 is illustrated as a disk-shaped cranial plate in these figures, but it is to be understood that the invention is contemplated to include bone plates 30 of varied configurations, such as linear, curved, T-shaped, Y-shaped, triangular, rectangular, square, circular or disk-shaped. Likewise, the configuration of the bone plate holder 10 may vary relative to the bone plate 30, as it is not essential that the configuration of the bone plate holder 10 mimic or correspond to the configuration of the bone plate 30, provided that the bone plate holder 10 is configured to retain a particular bone plate 30 in a manner that allows the bone plate 30 to be properly positioned and the mechanical fasteners 40 to be accurately driven through the bone plate 30 and into the bone. The bone plate 30 is composed of a substantially rigid material, such as titanium or other metal of similar properties, or of a resorbable polymer material, and is relatively thin in cross-section (typically 0.2 to 1.0 mm), as is well known in the art. The holder 10 is significantly thicker than the bone plate 30, such that it is easily grasped and manipulated by the surgeon using forceps or the like, and preferably corresponds generally in configuration to the configuration of the bone plate 30 for ease and accuracy in placing the bone plate 30. The bone plate 30 contains screw-receiving apertures 31 to receive the bone screws 40 for affixing the bone plate 30 to the bone material of the bone material, it being contemplated that equivalent mechanical fasteners such as rivets, tacks or the like could be substituted for the bone screws 40. As shown in the embodiment of FIGS. 1 through 4, the bone plate 30 may be disk-shaped and provided with five screw-receiving apertures 31, although it is to be understood that other shapes and configurations for the bone plate 30, as well as number and placement of screw-receiving apertures 31, are possible. For example, FIGS. 5 and 6 illustrate a bone plate 30 having a square configuration with a large interior open space.

Plate retainer means 20 are provided to temporarily mount and affix the bone plate 30 to the bottom 13 of holder 10, in a manner that allows the holder 10 to be easily and quickly removed from the bone plate 30 after the bone plate 30 has been affixed to the bone. Preferably, the mounting is accomplished be a mechanical interlock, press-fit or other friction technique operating between the holder 10 and the bone plate 30, although other means and methods such as the use of an adhesive or mechanical fasteners could be utilized. Alternatively, the bone plate 30 could be temporarily secured to the holder 10 by the interlocking of the bone screws 40 within the screw apertures 31. The bone plate 30 in FIGS. 1 through 4 is provided with a plurality of circular mounting apertures 32 that correspond to circular mounting nubs 21 of slightly greater diameter provided on the bottom 13 of the holder 10 that comprise the plate retainer means 20, such that the bone plate 30 my be press-fit onto the holder bottom 13 by aligning the mounting apertures 32 with the mounting nubs 21. The holder 10 is preferably constructed of a polymer material with slight resiliency relative to the material composing the bone plate 30 such that the press-fit mount is readily attained and easily disconnected.

Figure 1:
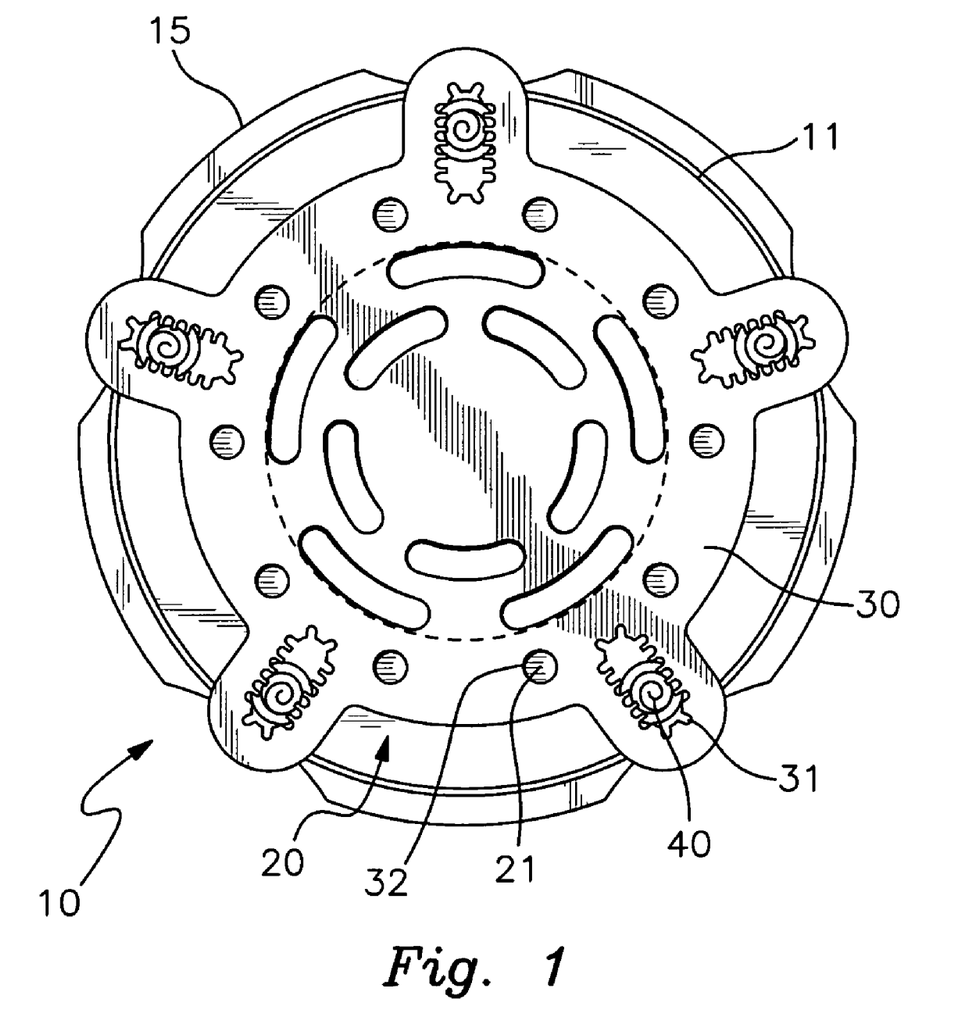
FIG. 1 is a bottom view of the invention, showing the bone plate and bone screws as retained on the holder device.
Figure 2:
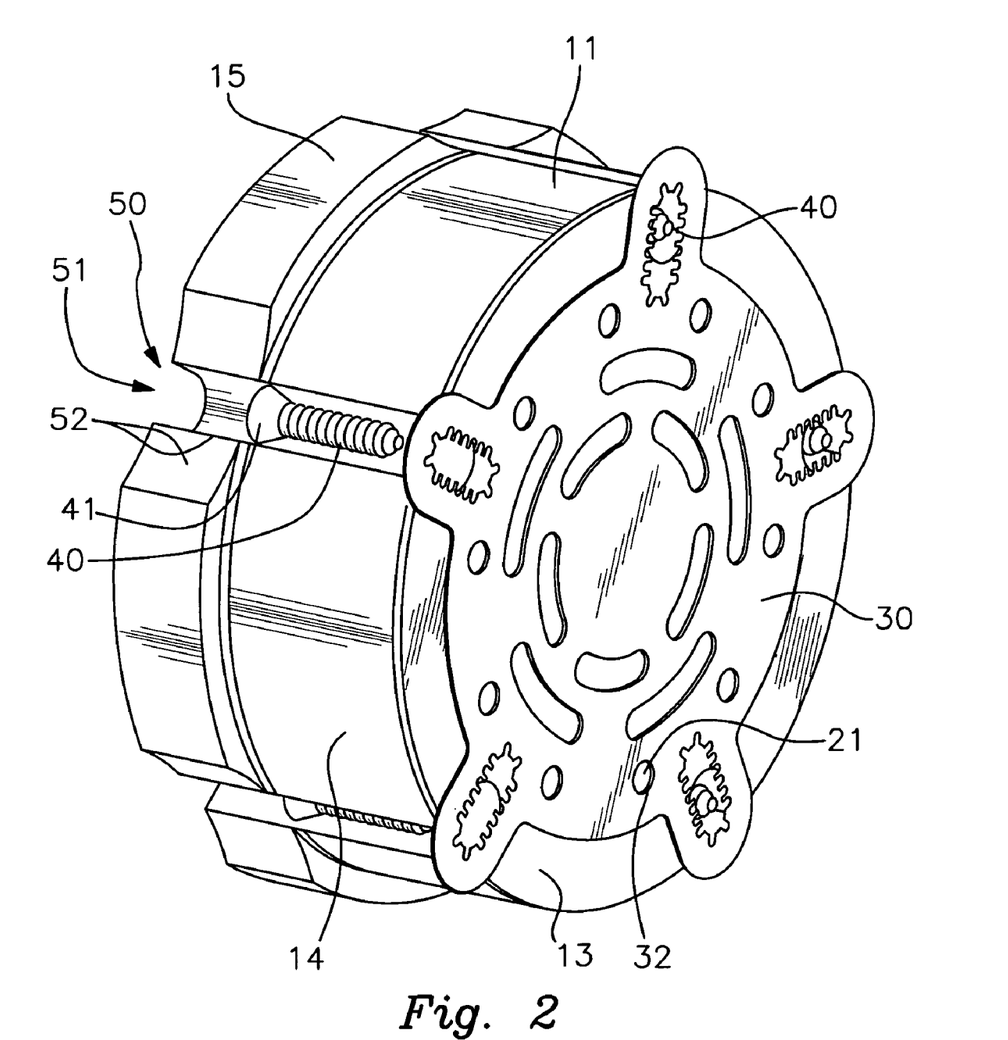
FIG. 2 is a perspective side view of the invention.
Figure 3:
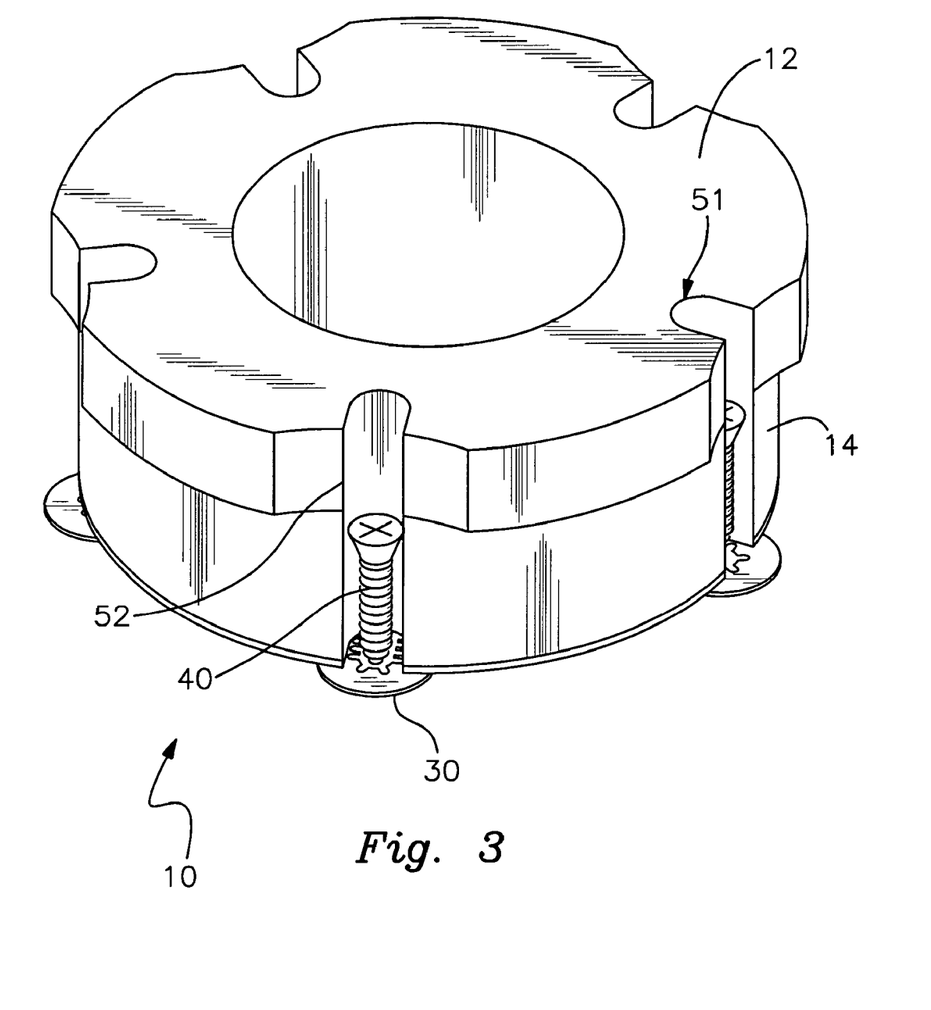
FIG. 3 is a side view of the invention.
Figure 4:
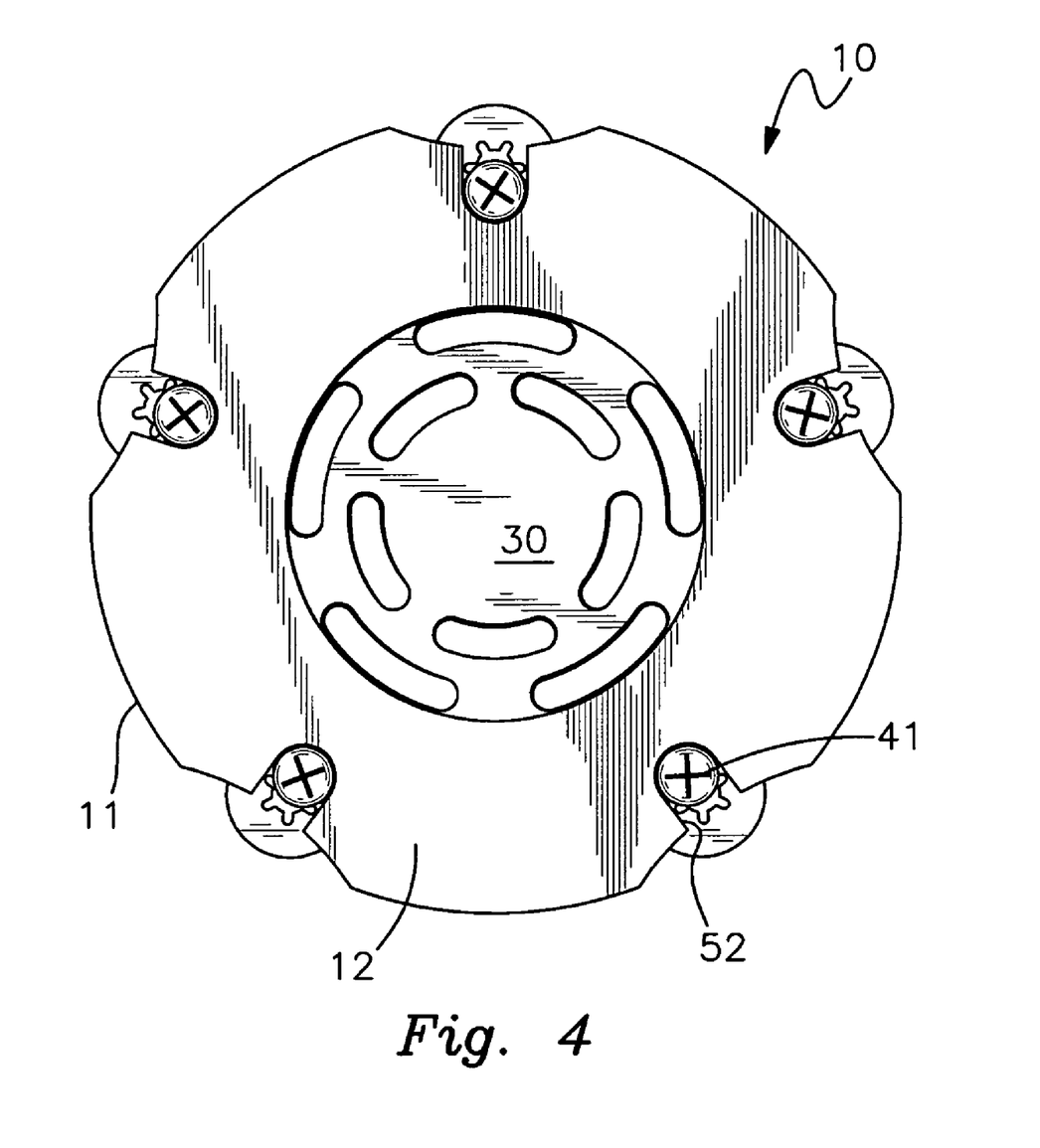
FIG. 4 is a top view of the invention.
Figure 5:
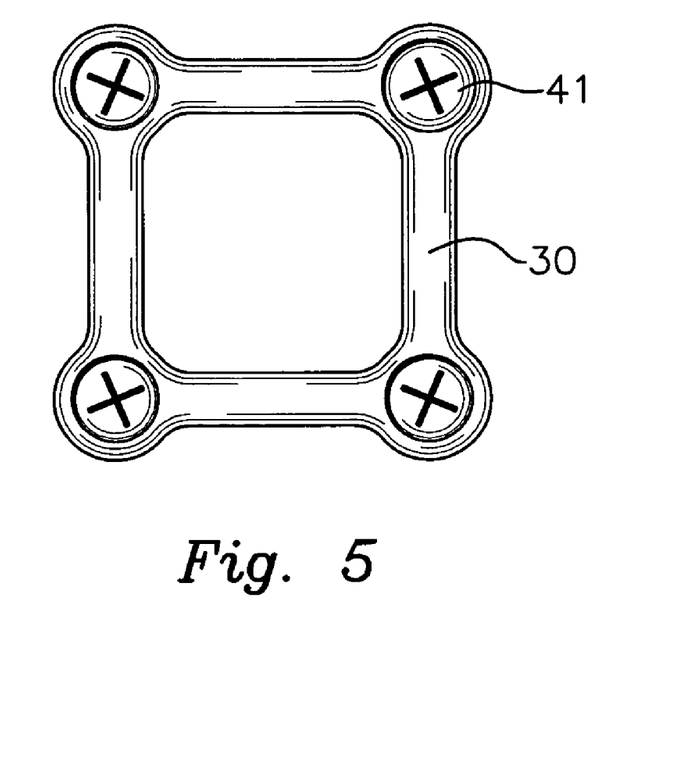
FIG. 5 is an exposed lateral view of an alternative embodiment of the invention.
Figure 6:
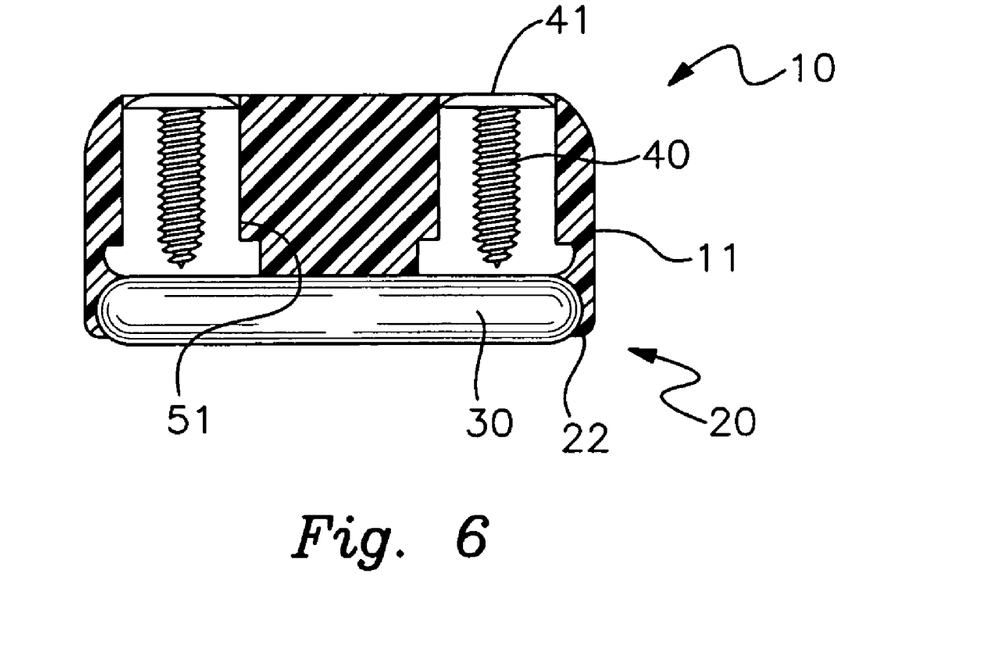
FIG. 6 is a top view of the bone plate and screws corresponding to the alternative embodiment of FIG. 5.

The holder 10 is provided with screw or equivalent mechanical fastener guide means 50, which as shown in FIGS. 1 through 6 comprise vertically oriented (i.e., perpendicular to holder bottom 13 and plate 30), substantially parallel passageways or bores 51 that are sized to correspond essentially with the circumference of the heads 41 of the screws 40, such that the screws 40 will be frictionally retained by the holder 10 when inserted into the guide bores 51 and aligned with the screw-receiving apertures 31 in the bone plate 30. Alternatively or in addition to the friction retention, the screws 40 may be retained within the guide bores 51 by application of an adhesive or structural retaining members, such as nubs or fingers disposed on the bore 51 above the screw 40, or with an additional cap member (not shown). The bores 51 may be non-perpendicular and non-parallel if required for particular applications. The fit of the screw heads 41 is sufficient to retain the screws 40 within the bores 51 while allowing the screws 40 to be turned with a relatively small amount of rotational force for implant into the bone material. The guide bores 51 further serve to properly orient the screws 40 and screw driving means relative to the bone plate 30 and the bone material, such that the screws 40 will not be driven at improper angles when affixing the plate 30 to the bone material. In an alternative embodiment, the diameter of the guide bores 51 may be increased over a short distance adjacent the bone plate 30, preferably a distance corresponding to the height of the screw heads 41 alone, such that the screws 40 are no longer frictionally retained by the bores 51 when the screws 40 have been fully inserted through the bone plate 30 and into the bone material, making removal of the holder 10 from the bone plate 30 easier, as shown in FIG. 5.

In a holder 10 having a substantially thick body, as shown in FIGS. 1 through 4, the guide bores 51 are preferably positioned adjacent the side 14 of the holder 10 so that a short portion of the bore circumference extends beyond the wall of the holder 10, thus creating an open slot 52 through which the surgeon can observe the position of the bone screws 40 during affixation. Alternatively, the holder 10 could be composed of a transparent or translucent material through which the screws 40 remain visible.

In FIGS. 5 and 6, an alternative embodiment of the invention is shown. FIG. 6 illustrates a bone plate 30 having a generally square configuration with four bone screws 40. The holder 10 has a bottom 13 corresponding to this configuration and four guide bores 51 corresponding with the screw 40 locations. In this embodiment, the plate retaining means 20 comprises a resilient shoulder 22 that snaps or clips onto the perimeter of the bone plate 30.

Figure 7:
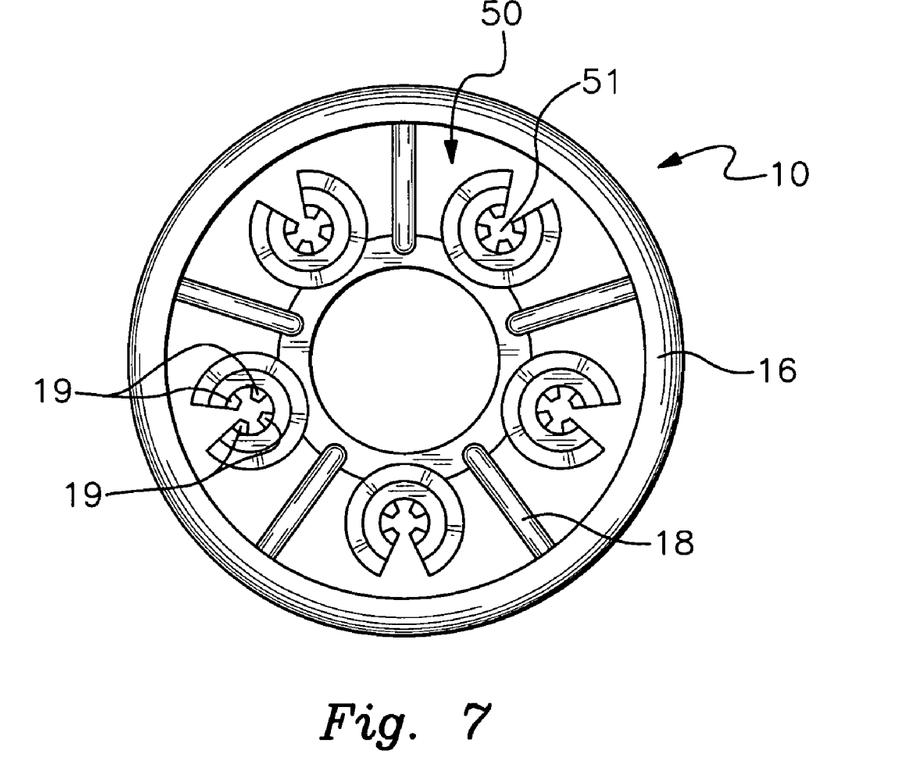
FIG. 7 is a top view of another alternative embodiment of the invention, wherein the holder comprises a framework rather than a relatively solid body.
Figure 8:
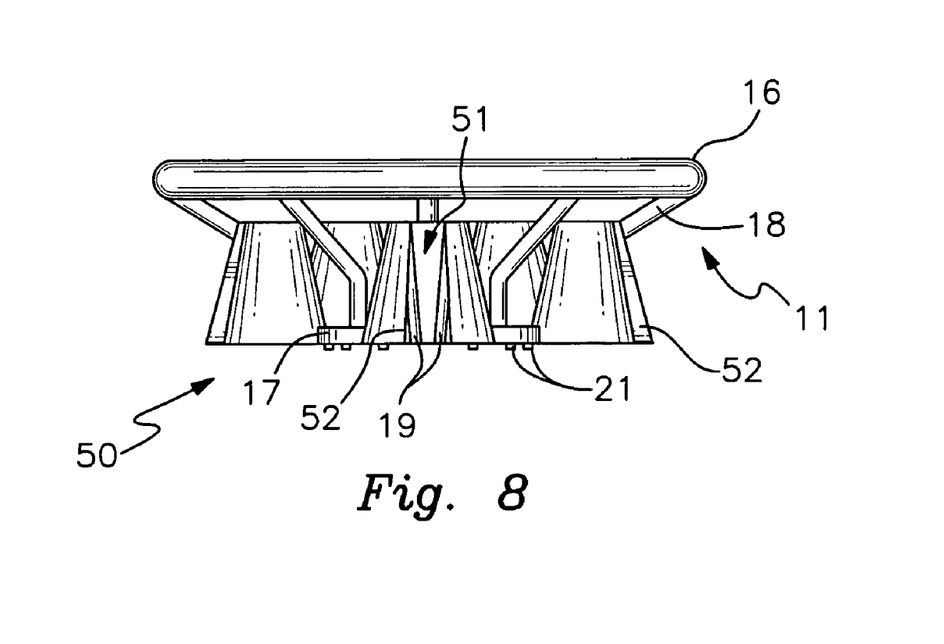
FIG. 8 is a side view of the embodiment of FIG. 7.
Figure 9:
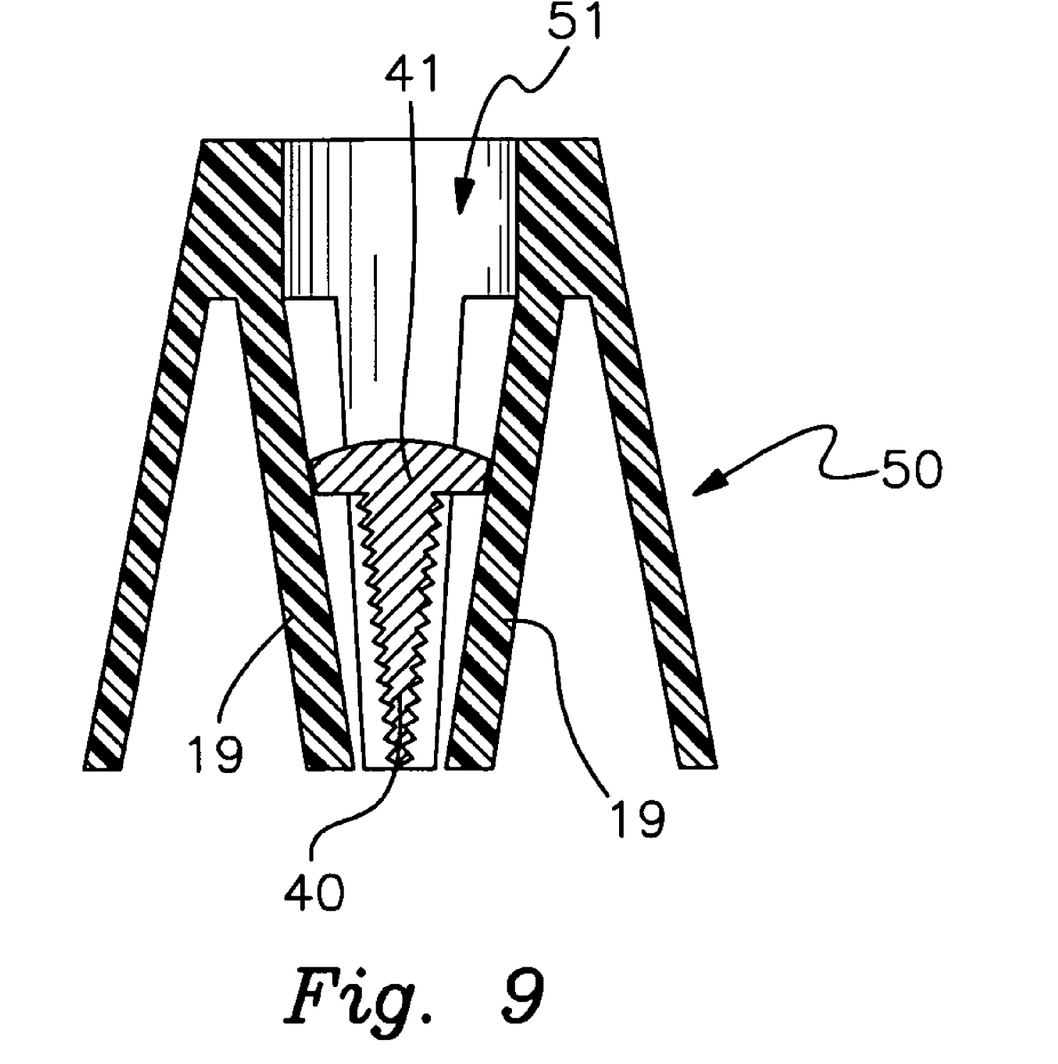
FIG. 9 is a cross-sectional view of one of the screw guide means of FIG. 7, showing a bone screw disposed in a guide bore.

In still another alternative embodiment, as shown in FIGS. 7 through 9, the main body 11 of the bone plate holder 10 comprises a framework structure rather than a substantially solid body. As illustrated, the main body 11 comprises an outer ring member 16 and an inner ring member 17 connected by strut members 18, where the outer ring member 16 is of greater diameter than the inner ring member 17 and is designed to be readily grasped by the surgeon. The screw guide means 50 are individually mounted about the inner ring member 17 and the bore 51 to receive and retain the screw 40 is a straight or tapered bore defined by a plurality of depending finger members 19 that flex radially outward as the bone screw 40 is advanced into the bone plate during application. Slots 52 may be provided for visual identification as to the location of the bone screws 40 within the screw guide means 50.

In the preferred embodiment the bone plate holder 10 is substantially rigid, but in an alternative embodiment the holder 10 is composed of a slightly flexible polymer material such the surgeon may apply compressive force against the holder 10 to flex the bone plate 30 in circumstances where the contour of the bone surface is not planar, either prior to initiating the attachment procedure or after the bone plate 30 has been properly positioned on the bone.

To use the invention, the surgeon grasps the sides 14 of the holder device 10 by hand, or by using forceps or similar means, and positions the bone plate 30 retained on the holder bottom 13 at the desired location on the bone for affixation, with the bone screws 40 being disposed on opposites sides of the junction or kerf in the bone material or sufficient distance beyond the perimeter of a bone hole. Since the screws 40 are already disposed in the guide bores 51, individual screws 40 do not need to be grasped, inserted in the bone plate 30, properly aligned and then driven. A screwdriver means is then inserted longitudinally into the guide bores 51 and each screw 40 is driven into the bone material. The guide bores 51 insure that the driver means and each screw 40 are properly oriented and aligned. With all the screws 40 fully inserted and the bone plate 30 securely affixed to the bone, the holder 10 is removed be applying sufficient retraction force to overcome the retentive force of the plate retainer means 20.

The holder 10 can also be utilized as a guide for the insertion of bone screws 40 without mounting a bone plate 30 onto the bottom 14 of the holder, since the guide bores 51 maintain the screws 40 in proper alignment during insertion.

It is contemplated that equivalents and substitutions for certain elements set forth above may be obvious to those skilled in the art, and therefore the true scope and definition of the invention is to be as set forth in the following claims.

We claim:

1. A bone plate to bone material affixing system comprising:
   a holder comprising screw guide means temporarily retaining and aligning for proper insertion bone screws adapted to affix a bone plate to bone material, and further comprising bone plate retainer means temporarily retaining a bone plate;
   a bone plate releasably mounted to said holder, said bone plate comprising screw receiving apertures to receive said bone screws; and
   bone screws having screw heads, said bone screw heads being disposed within said screw guide means, wherein said screw guide means are sized such that said bone screw heads pass completely through said holder when fully inserted into said screw receiving apertures of said bone plate, whereby said bone plate is affixed to bone material by said bone screws, and further wherein said holder is removable from said bone plate when said bone plate is so affixed wherein said screw guide means comprise a plurality of bores, and wherein the diameter of said bores essentially corresponds to the diameter of said screw heads, such that said screws are frictionally retained within said bores.

2. The system of claim 1, wherein the diameter of a portion of said bores adjacent said bone plate is increased over a distance at least corresponding to the height of the bone screw heads.

3. The system of claim 1, wherein said bores each comprise an exposed slot.

4. The system of claim 1, wherein said bone plate is frictionally retained by said holder.

5. The system of claim 1, wherein said bone plate is retained by said holder by mechanical interlocking.

6. The system of claim 1, said bone plate further comprising mounting apertures, wherein said bone plate retainer means comprises a plurality of mounting nubs disposed on said holder and corresponding to said mounting apertures.

7. The system of claim 1, wherein said holder and said bone plate have corresponding configurations.

8. The system of claim 1, wherein said holder is composed of a polymer material.

9. The system of claim 1, wherein said holder is composed of a translucent material.

10. The system of claim 1, wherein said holder is composed of a transparent material.

11. The system of claim 1, wherein said holder is composed of a flexible polymer.

12. The system of claim 1, wherein said holder comprises a framework and said screw guides means are mounted onto said framework.

13. The system of claim 12, wherein said screw guide means comprise a plurality of finger members defining a bore to receive said bone screws.

14. The system of claim 13, wherein said bore defined by said finger members is tapered.

15. The system of claim 14, wherein said framework comprises an outer ring member and an inner ring member connected by strut members, and wherein said screw guide members are mounted on said inner ring member.

16. A holder device for retaining a bone plate and mechanical fasteners, whereby the bone plate may be affixed to a bone material by inserting said mechanical fasteners through said bone plate and into said bone material while said holder device is maintained in a chosen position, the device comprising:
   a main body:
   bone plate retainer means to temporarily retain said bone plate on said main body: and
   guide means to temporarily retain and properly orient said mechanical fasteners, wherein said guide means are sized such that said mechanical fasteners pass completely through said holder device upon insertion of said mechanical fasteners into said bone plate without securing said holder to said bone plate;
   said bone plate further comprising mounting apertures, wherein said bone plate retainer means comprises a plurality of mounting nubs disposed on said holder and corresponding to said mounting apertures.

17. The device of claim 16, wherein said guide means comprise a plurality of bores extending through said main body.

18. The device of claim 17, wherein said mechanical fasteners comprise screws having screw heads and wherein the diameter of said bores essentially corresponds to the diameter of said screw heads, such that said screws are frictionally retained within said bores.

19. The device of claim 18, wherein the diameter of said bores is increased over a distance at least corresponding to the height of the screw heads.

20. The device of claim 17, wherein said bores each comprise an exposed slot.

21. The device of claim 16, wherein said bone plate is frictionally retained by said holder.

22. The device of claim 16, wherein said bone plate is retained by said holder by mechanical interlocking.

23. The device of claim 16, wherein said holder is composed of a polymer material.

24. The device of claim 16, wherein said holder is composed of a translucent material.

25. The device of claim 16, wherein said holder is composed of a transparent material.

26. The device of claim 16, wherein said holder is composed of a flexible polymer.

27. The device of claim 16, wherein said main body comprises a framework and said guides means are mounted onto said framework.

28. The device of claim 27, wherein said guide means comprise a plurality of finger members defining a bore to receive said mechanical fasteners.

29. The device of claim 28, wherein said bore defined by said finger members is tapered.

30. The device of claim 29, wherein said framework comprises an outer ring member and an inner ring member connected by strut members, and wherein said screw guide members are mounted on said inner ring member.

31. A system for affixing a bone plate to bone material comprising:

bone screws having screw heads;

a holder comprising screw guide means to temporarily retain and align said bone screws and bone plate retainer means to retain a bone plate, said screw guide means comprising a plurality of bores each having a diameter essentially equal to or greater than the diameter of said screw heads, such that said bone screw heads are not precluded from passing completely through said holder;

a bone plate releasably mounted to said holder, said bone plate comprising screw-receiving apertures corresponding in location to said bores; and bone screws disposed within said bores whereby said bone screws are aligned to pass through said screw-receiving apertures of said bone plate wherein the diameter of said bores essentially corresponds to the diameter of said screw heads, such that said screws are frictionally retained within said bores.

32. The system of claim 31, wherein the diameter of a portion of said bores adjacent said bone plate is increased over a distance at least corresponding to the height of the bone screw heads.

33. The system of claim 31, wherein said bores each comprise an exposed slot, whereby said bone screws are visible externally.

34. The system of claim 31, wherein said bone plate is frictionally retained by said holder.

35. The system of claim 31, wherein said bone plate is retained by said holder by mechanical interlocking.

36. The system of claim 31, said bone plate further comprising mounting apertures, wherein said bone plate retainer means comprises a plurality of mounting nubs disposed on said holder and corresponding to said mounting apertures.

37. The system of claim 31, wherein said holder and said bone plate have corresponding configurations.

38. The system of claim 31, wherein said holder is composed of a polymer material.

39. The system of claim 31, wherein said holder is composed of a translucent material.

40. The system of claim 31, wherein said holder is composed of a transparent material.

41. The system of claim 31, wherein said holder is composed of a flexible polymer.

42. The system of claim 31, wherein said holder comprises a framework and said screw guides means are mounted onto said framework.

43. The system of claim 42, wherein said screw guide means comprise a plurality of finger members defining said bore.

44. The system of claim 43, wherein said bore defined by said finger members is tapered.

45. The system of claim 43, wherein said framework comprises an outer ring member and an inner ring member connected by strut members, and wherein said screw guide members are mounted on said inner ring member.

46. The system of claim 31, wherein said screw guide means releasably retain said bone screws, and whereby upon affixation of said bone plate to bone material, said holder is separable from said bone screws and said bone plate.

* * * * *